United States Patent [19]
Kanan et al.

[11] Patent Number: 6,132,975
[45] Date of Patent: *Oct. 17, 2000

[54] METHOD OF COLLECTING MARKERS OF BONE METABOLISM FROM SWEAT

[75] Inventors: Paul G. Kanan, Laguna Niguel, Calif.; Richard H. Smith, Dexter, Mich.; Ellen Rudnick, Deerfield, Ill.

[73] Assignee: Bioquant, Inc., Ann Arbor, Mich.

[ * ] Notice: This patent is subject to a terminal disclaimer.

[21] Appl. No.: 08/777,532

[22] Filed: Dec. 30, 1996

Related U.S. Application Data

[63] Continuation-in-part of application No. 08/263,137, Jun. 21, 1994, Pat. No. 5,589,346.

[51] Int. Cl.$^7$ ..................................................... G01N 33/53
[52] U.S. Cl. ........................ 435/7.1; 435/7.92; 435/967; 435/973; 436/86; 436/174; 436/501; 436/518; 436/811; 436/813; 436/815; 422/50; 422/56; 422/61
[58] Field of Search ..................................... 435/7.1, 7.92, 435/967, 973; 436/86, 174, 501, 518, 811, 813, 815; 422/50, 56, 61

[56] References Cited

U.S. PATENT DOCUMENTS

| | | | |
|---|---|---|---|
| 4,957,108 | 9/1990 | Schoendorfer et al. | 128/632 |
| 4,973,666 | 11/1990 | Eyre | 530/323 |
| 5,076,273 | 12/1991 | Schoendorfer et al. | 128/632 |
| 5,140,103 | 8/1992 | Eyre | 530/327 |
| 5,203,327 | 4/1993 | Schoendorfer et al. | 128/632 |
| 5,283,197 | 2/1994 | Robins | 436/87 |
| 5,661,039 | 8/1997 | Kung et al. | 436/501 |

OTHER PUBLICATIONS

Bettica et al., "Bone–resorption markers galactosyl hydroxylysine, pyridinium crosslinks, and hydroxyproline compared" *Clin. Chem.*, 38:2313–8 (1992).
Body et al., "Urinary pyridinium cross–links as markers of bone resorption in tumor–associated hypercalcemia" *J. Clin. endocrin Metab.* 74:471–5 91992).
Delmas, PD "Biochemical markers of bone turnover: methodology and clinical use in osteoporosis" *Am. J. Med.*, 91 (Supp 5B): 59S–63S (1991).
Delmas et al., "Urinary excretion of pyridinoline crosslinks correlates with bone tulrnover measured on iliac crest biopsy in patients with vertebral . . . " *J. Bone Miner Res.*, 6:639–44 (1991).
Eastell et al., "Nyctohemeral changes in bone turnover assessed by serum bone gla–protein concentration and urinary deoxypyridinoline excretion: effects of growth adn aging" *Clin. Sci.* 83:375–82 (1992).
Eastell et al., "Abnormalities in circadian patterns of bone resorption adn renal calcium conservation in type I osteoporosis" *J. Clin. Endocrin Metab.* 74:487–94 (1992).
Eloma et al., "Serum concent5ration of the cross–linked carboxyterminal telopeptide of type I collagen (ICTO ( us a useful prognostic indicator in multiple . . . " *Br. J. Cancer* 66:37–41 (1992).
Eyre, Collagen cross–linking amino acids in *Methods Enzymol.*, 114:115–139 (1992).
Gertz et al., "Monitoring bone resprption in early postmenopausal women by an immunoassay for crosslinked collagen peptides in urine" *J. Bone Min. Res.*, 9:135–142 (1994).
Gomez et al., Monoclonal antibody assay for free urinary pyridinium cross–links, *Clin. Chem.*, 42:1168–1175 (1996), *Eur. J. Clin. Invest.*, 21:310—5 (1991).
Harvey et al., "Measurement of bone collagen degradation in hyperthyroidism and during thyroxine replacement therapy using pyridinium . . . ", *J. Clin. Endocrin. Metab.*, 72:1189–94 (1991).
Robins et al., "Evaluation of urinary hydroxypridiniym crosslink measurements as resorption markers in metabolic bone diseases" *Eur. J. Clin. Invest.*, 21:310–5 (1991).
Rosen et al., "Specificity of urinary excretion of cross–linked N–telopeptides of Type I collagen as a marker of bone turnover", *Calcif. Tiss. Int.*, 54:26–29 (1994).
Schlemmer et al., "Marked diurnal variation in urinary excretion of pyridinium cross–links in premenopausal women", *J. Clin., Endocrin Metab.*, 74:476–80 (1992).
Seibel et al., "Urinary hydroxypyridinium crosslinks provide indices of cartilage adn bone involvement in arthritic diseases", *J. Rheumatol.*, 16:964–970 (1989).
Robins et al., "Measurement of the compound, pyridinoline, in urine as an index of collagen degradation in joint disease," *Annals of the Rheumatic Diseases*, vol. 45, pp. 969–973 (1986).

*Primary Examiner*—Jeffrey Stucker
*Attorney, Agent, or Firm*—Knobbe, Martens, Olson & Bear, LLP

[57] ABSTRACT

The invention disclosed herein relates to a method of monitoring bone metabolism comprising continuously collecting a sweat sample from a subject and assaying the sweat sample to determine the concentration of a marker of bone metabolism in the sample, wherein said marker is not pyridinoline or deoxypyridinoline.

22 Claims, 7 Drawing Sheets

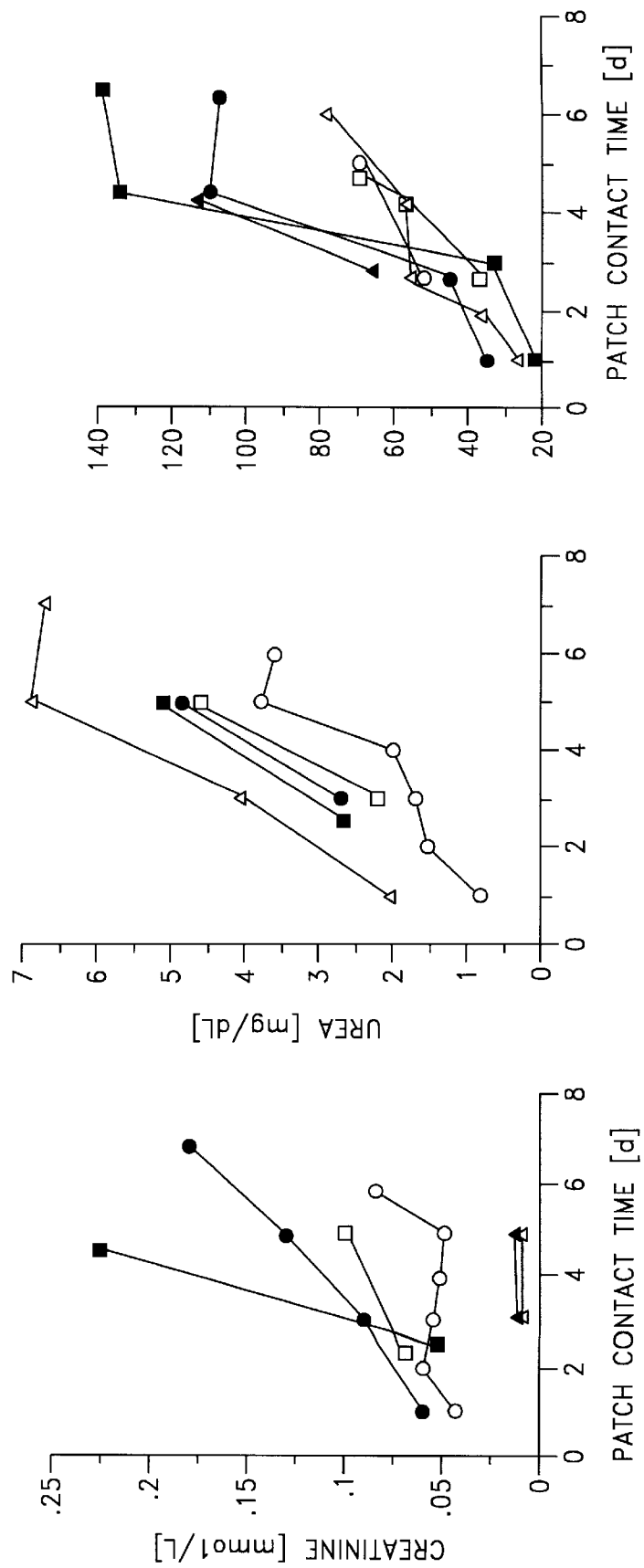

METHOD OF COLLECTING MARKERS OF BONE METABOLISM FROM SWEAT

This is a continuation-in-part of application Ser. No. 08/263,137 filed on Jun. 21, 1994 U.S. Pat. No. 5,589,346.

TECHNICAL FIELD

The present invention relates to a method for detecting markers of bone metabolism. More particularly, the present invention relates to method for collecting and analyzing sweat for the presence of markers of bone metabolism.

DESCRIPTION OF RELATED ART

Current methods used to monitor the presence, progress of treatment, or disease state for metabolic bone diseases require the measurement of markers of bone metabolism found in blood or urine samples. Examples of these methods are shown in U.S. Pat. No. 5,283,197 to Robins, U.S. Pat. No. 4,973,666 to Eyre, and U.S. Pat. No. 5,140,103 also to Eyre. The most commonly measured of these markers include calcium, hydroxyproline, alkaline phosphatase, procollagen Type I and its cleavage products, osteocalcin, and bone collagen peptides that include crosslinked amino acids. The crosslinked amino acids include pyridinoline, hydroxy lysyl pyridinoline, lysyl pyridinoline, N-telopeptide, and the peptides that contain the former molecules.

These molecules are specific collagen breakdown products known to be produced following bone resorption. Thus, the measurement of these crosslinked amino acids (markers of bone metabolism) can provide an indication of metabolic bone disease, and can be of use in monitoring the progress of medical treatment intended to reduce the loss of bone density found in various disease states.

As with many other molecules of biological interest, the production of crosslinked amino acids varies over time in a diurnal cycle (Schemer et al., 1992, Easel et al., 1992, Easel et al, 1992) and can also vary in concentration from day-to-day (Hertz et al. 1994). Normal biological variations in the concentration of these collagen breakdown products in healthy individuals can nearly equal the levels of these molecules that are obtained in individuals with diagnosed disease states typified by high levels of metabolic bone loss over extended periods of time. Such disease states include diseases such as osteoporosis (Betake et al., 1992, Deltas, 1991), hyperparathyroidism (Harvet et al., 1991, Robins et al., 1991), Paget's disease (Bettica et al., 1992, Robins et al., 1991), rheumatoid arthritis (Seibel et al., 1989), multiple myeloma (Elomaa et al., 1992), tumor-associated hypercalcemia (Body et al., 1992) and osteoarthritis (Elomaa et al., 1992, Delmas et al., 1991). The above-cited U.S. patents to Robins and Eyre describe methods for analyzing urine and blood samples in order to assay for levels of indicators of bone loss. However, the collection of a single blood or urine sample is representative of only a single point in time, therefore, any variation in the levels of markers of bone metabolism may not be discovered due to the natural diurnal and day-to-day variations in concentration inherent with these markers. Additionally, these prior art methods typically require the services of a technician, such as someone to draw a blood sample or these prior methods may require the subject go to a laboratory, a hospital or a doctor's office in order to submit a sample for analysis. This can be problematic where a subject must submit a series of successive samples for analysis in order to obtain enough test results to allow for a meaningful diagnosis. That is, since the results derived from the prior art methods are representative of only a single point in time; the subject must submit multiple blood or urine samples in order reduce the possibility that he/she will receive a false positive or false negative test result. This problem is not only one of inconvenience, but also represents a significant cost to the subject and the potential for misdiagnosis.

In order to overcome the problems associated with the prior art method of analysis, it is necessary that a modality of collection be introduced which eliminates the biological variations due to diurnal and day-to-day variations by providing a means of collection which is continuous and uninterrupted thereby allowing for the collection of a more meaningful sample which has the benefit of being integrated over time to reduce the effects of biological variations in bone loss marker production. Additionally, the method should also increase the diagnostic power of the test by reducing the incidence of false positive and false negative test results.

The present invention not only eliminates some of the burden and inconvenience associated with the prior art methods, it yields the added benefits of improved accuracy and performance by eliminating certain long-standing problems such as biological variation, thereby making the measurement of the bone loss marker more meaningful and greatly increases its significance in diagnosis and treatment of bone resorption disease states. The Applicant has found that markers of bone metabolism (collagen breakdown products) are present in sweat in detectable levels which are indicative of physiological bone loss. Additionally, applicants have found that by collecting a sample of sweat over a period of time, quantifiable results can be obtained which provide for a more accurate and representative assessment of bone resorption.

The subject invention describes the use of a skin patch for the collection of perspiration or sweat which collects a sample for analysis in which the diurnal and day-to-day variations of crosslinked amino acids is minimized. Perspiration or sweat collected over a period of days accumulates in a sample that minimizes the sources of biological variation through integration over time, making the measurement of the bone loss marker more meaningful value and thereby increasing its significance in the diagnosis and treatment of disease states. The use of the skin patch also provides a means for specimen collection that can be performed at clinics, in a physician's office, or at home, thus, it is suitable for monitoring the efficacy of therapeutic regimens for metabolic bone disease and can be used in screening for the onset or the progression of bone diseases.

SUMMARY OF THE INVENTION

In accordance with the present invention, there is provided a method of monitoring markers of bone metabolism by continuously collecting a body fluid sample containing markers of bone metabolism therein and analyzing the components of the body fluids for the markers of bone metabolism.

FIGURES IN THE DRAWINGS

Other advantages of the present invention will be readily appreciated as the same becomes better understood by reference to the following detailed description when considered in connection with the accompanying drawings wherein:

FIG. 7 is a graph showing the relationship of the concentration of creatinine collected in sweat as a function of time, skin patches were worn concurrently for 1 to 7 days by six subjects and were then extracted and creatinine was measured in each extract;

FIG. 8 is a graph showing the relationship of the concentration of urea collected in sweat as a function of time, skin patches were worn concurrently for 1 to 7 days by six subjects and patches were extracted and urea was measured in each extract;

FIG. 9 is a graph showing the relationship of the concentration of potassium collected in sweat as a function of time, skin patches were worn concurrently for 1 to 7 days by six subjects and were then extracted and potassium was measured in each extract by use of an ion selective electrode;

Figure 11B:
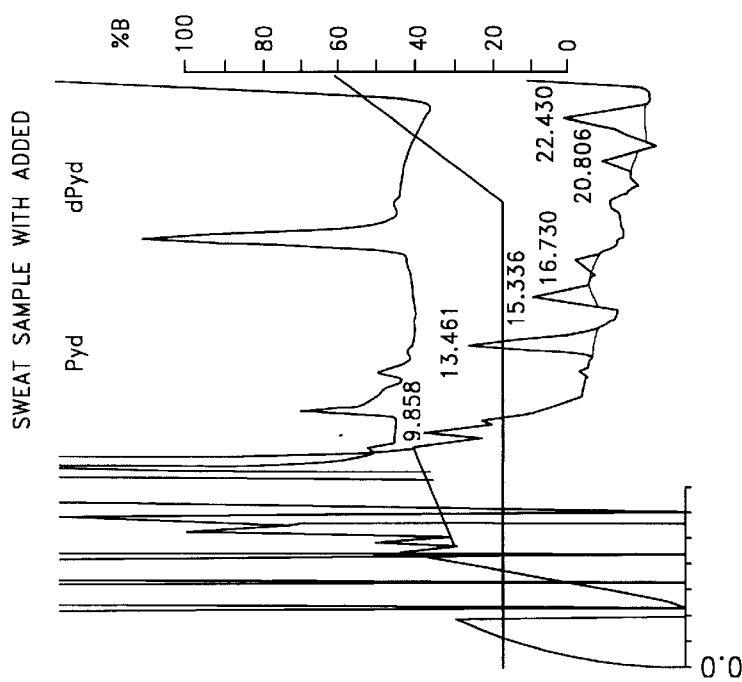
Figure 11A:
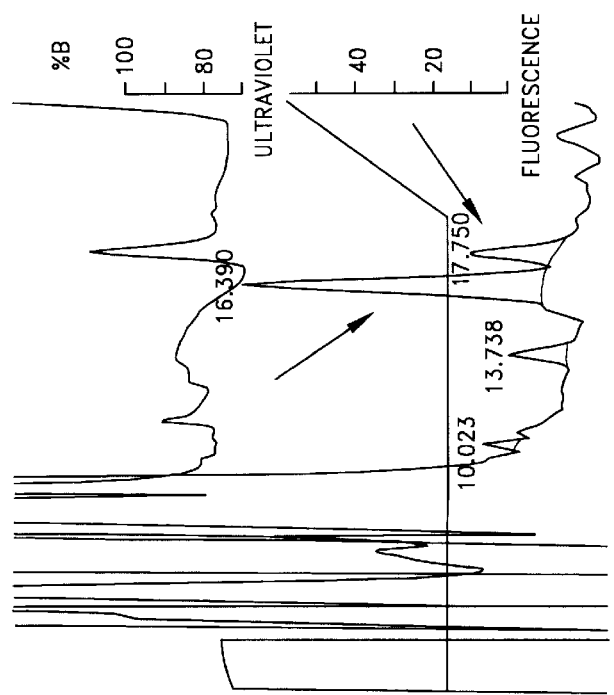
Figure 12:
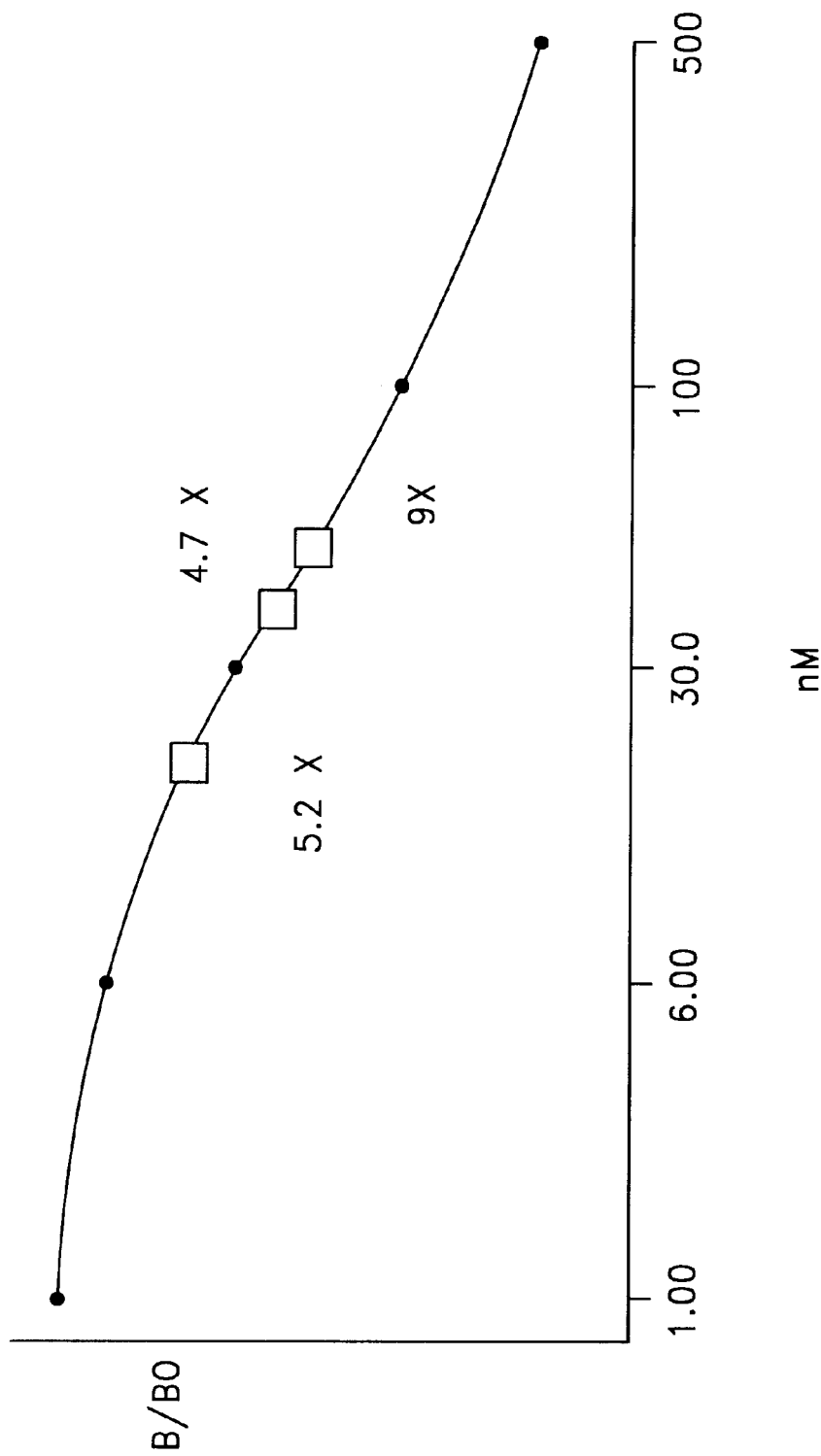

FIGS. 11A–B illustrates HPLC tracings confirming the presence of deoxypyridinoline in sweat wherein (A) shows a sweat sample after being re-injected for a second HPLC separation after known amounts of standard pyridinoline and deoxypyridinoline were added (spiked) to the sample and (B) shows the same sweat sample as in (A) illustrating the presence of two peaks identified as pyridinoline and deoxypyridinoline based on their co-migration with pyridinoline and deoxypyridinoline HPLC standards; and FIG. 12 is a graph illustrating a standard curve in a specific enzyme-linked immunoassay for for N-telopeptide wherein ■ represent the location on a standard curve of three concentrated (lyophilized) sweat samples.

DETAILED DESCRIPTION OF THE INVENTION AND ADVANTAGES

The present invention provides a method for monitoring markers of bone metabolism in a sample of bodily fluid continuously collected over a period of time. The subject invention provides a method of continuously collecting a bodily fluid, such as sweat, over a period of time in order to collect a sweat sample containing markers indicative of diseases involving bone loss or resorption or which indicate normal levels of bone metabolism (i.e., normal growth and death of bone). The collected sweat sample, then, can be analyzed to determine the presence of these markers of bone metabolism and thereby ascertain possible disease states or conditions.

The continuous collection of a bodily fluid is defined as the uninterrupted collection of a bodily fluid over a given period of time. A sample of a bodily fluid is collected over a period of time without any gaps or breaks in the collection of the sample. This is unlike a typical blood or urine sample which is only representative of the point in time in which the sample was taken. Continuous and uninterrupted collection of a bodily fluid allows for the analysis of a sample which is representative of a period of time and, therefore, diurnal and other variations over time can be reduced, eliminated, or controlled.

The continuous and uninterrupted collection of a one week long sweat sample for analysis poses a novel and, somewhat less cumbersome method than collecting a one week long total urine sample. The continuous and uninterrupted collection of sweat can be done without any subject participation and, therefore, subject compliance can be greatly enhanced. In other words, all the subject must do is either apply a collection device or have a collection device applied at the beginning of the sampling period and wear the collection device for the prescribed collection period. After application of the device, the subject is required to do nothing else except function normally. Unlike collecting total urine samples or successive blood sampling, the subject need only visit his or her clinician at the beginning of the collection period for application of the device and at the end of the collection period for removal and analysis of the sample collected in the device. Alternatively, the subject can apply and/or remove the device themselves. Therefore, this minimal amount of subject participation greatly increases the subject compliance with the sample collection and analysis thereof.

Perspiration is defined as the functional secretion of sweat due to the secretory activity of sweat glands. Sweat is the liquid secreted by the sweat glands and primarily contains water and sodium chloride. However, sweat can also contain other compounds or analytes present in trace, but detectable, amounts such as urea, albumin and markers of bone metabolism.

Generally, in order to collect a sweat sample, a sweat collection device is applied to a subject to be tested. The sweat collection device can be any device suitable for the collection of sweat or perspiration which is also designed such that the aqueous component (i.e. water) is allowed to evaporate from the collection device leaving behind only non-volatile matter attached to or trapped within an absorbent pad disposed within the device. That is, in order to more precisely maintain normal sweat or perspiration rates, the collection device must allow the aqueous component of the sweat to evaporate normally. Any collection device which alters the normal evaporation of sweat or gas exchange of the skin with its surroundings may induce or lead to the production of inaccurate data due to abnormal or induced physiological response of the skin to the artificial environment created by the application of the collection device.

Typical sweat collection devices include an adsorbent pad such as a cotton gauze, synthetic pad, other permeable materials, a capillary tube, or skin patch devices, such as those described in U.S. Pat. Nos. 4,957,108, 5,076,273, and 5,203,327 all to Schoendorfer et al. and all assigned Sudor Partners, Inc., all of which are incorporated herein by reference. The sweat collection devices disclosed in these patents are all trans-dermal sweat collection devices which allow for the collection of one or more analytes in a bodily fluid expressed through the skin to be collected in a patch and concentrated by active and passive driving off a substantial portion of the water fraction under the influence of body heat (active) and air evaporation (passive). Said another way, these sweat collection devices allow for the recovery of the analytes present in the sweat while allowing for the normal evaporation of fluids and gas exchange of the skin with the surrounding atmosphere.

Each of the devices described in the Schoendorfer et al. references refers to a trans-dermal sweat collection patch which contains an absorbent pad for collection of analytes present in the collected sweat samples which is affixed to the subject by means of an adhesive such as adhesive tape or other means known to those skilled in the art. Analytes present in the sweat samples are deposited on the absorbent pad and the aqueous and volatile contents of the sweat are eliminated by evaporation and normal gaseous exchange with the environment, respectively.

The sweat collection patches are applied over the prepared area of skin and are worn by the subject for a prescribed collection time period.

After the patch has been worn for a sufficient period of time, the patch is removed from the subject and is prepared for analysis. The absorbent pad is separated from an adhesive backing and is prepared for analysis by placing the absorbent pad into a vacuum desiccator to ensure uniform dehydration. The analytes, i.e. markers of bone metabolism, are then extracted from the absorbent pad in a suitable extraction buffer in order to remove the analytes containing the markers of bone metabolism from the pad area by methods described below.

Markers of bone metabolism include any products produced or given off during normal or abnormal growth and/or death of bone. These markers of bone metabolism can be used to determine normal, healthy conditions as well disease states. The markers of bone metabolism may be any of a group including crosslinked amino acids, such as pyridinoline, hydroxy lysyl pyridinoline, lysyl pyridinoline, substituted pyridinolines, N-telopeptide, procollagen Type I and its cleavage products, and osteocalcin. Some preferred markers for use in the method of the present invention include pyridinoline and N-telopeptide since they are compounds known to be indicative of bone resorption and are present in the sweat in amounts which are detectable and representative of resorptive bone diseases. However, the other markers described below are also indicative of bone metabolism and when viewed in light of the examples set forth below, cover a number of the known markers of bone metabolism.

Pyridinoline, deoxypyridinoline, and N-telopeptide are markers which indicate bone-loss. These markers are catabolic products derived from the enzymatic digestion of bone-type collagen by a specialized bone degrading cell, i.e., osteoclasts. The peptides produced by osteoclasts are further degraded to free cross-links (pyridinoline and deoxypyridinoline) in blood, liver, and predominately in the kidney. The presence of these molecules in blood, urine, and sweat indicates that bone loss or remodeling is occurring.

After the markers of bone metabolism, i.e., pyridinoline, have been extracted from the absorbent pad, the extract containing the markers of bone metabolism is analyzed by enzyme immuno-assay (EIA), HPLC, or by any other method well known in the art which is capable of quantitatively and/or qualitatively detecting the presence of desired markers, in order to quantitatively determine the concentration of the bone loss marker and qualitatively determine the presence of markers of bone metabolism.

In order to more accurately determine the concentration of the bone loss marker present in a given sweat sample, the volume of sweat is normalized by quantitatively analyzing the concentration of a reference marker in the sweat collected concurrently with the sweat sample from the subject. The reference marker may be any analyte secreted transdermally at a relatively constant and known rate. Such a reference analyte can typically include creatinine, urea, potassium or any other analyte secreted at a constant rate. By quantitatively measuring the concentration of a specific reference marker, it is possible to determine the volume of sweat which has been transdermally secreted over the given collection period. Knowing the approximate volume of sweat secreted during this time period provides an accurate estimate of the volume of sweat collected thereby allowing an accurate calculation of the concentration of the bone loss marker present in the sample. Therefore, a quantitative value for the concentration of a bone loss marker, integrated over a given time period, is obtained which is free of diurnal and day-to-day variations. This method provides for the continuous and uninterrupted collection of a sample over a period of time which eliminates the uncertainty and variability associated with a "point in time" sampling method such as a blood or urine analysis.

EXAMPLES

Materials and Methods

REAGENTS

From Sigma Chemical Co. (St. Louis, Mo.) sodium phosphate, thimerosal, Triton X-100, Tween 20 and assay kits for the determination of creatinine and urea. The osmolarity of samples was measured by use of a vapor pressure osmometer (Wescor model 5500, Logan Utah).

SWEAT SAMPLE COLLECTION

The area of the skin to which skin patches were applied was wiped for ~30 seconds with a sterile alcohol prep pad (Professional Disposables, Inc., Orangeburg, N.Y.), and the skin was allowed to dry completely (~2 min.) before patch application. Care was taken not to touch the absorbent pad of the skin patch at any time. Patches were applied by stretching the skin slightly to eliminate wrinkles. Each patch was placed over the prepared area and was smoothed from the center toward the periphery. The time of skin patch application was recorded, and patches typically were removed at 24 hour intervals, ±½ hour. Pads were separated from their adhesive backing and were stored in plastic bags at 4° C.

EXTRACTION

Skin patches (Sudormed, Inc., Santa Ana, Calif.) were dried in a vacuum desiccator overnight to assure uniform hydration. The patches were placed in 3 mL syringes (Becton Dickinson Company, Rutherford, N.J.) along with 1.0 mL (1.0–2.5 ml) of the extraction buffer (EB; 10 mM $NaPO_4$ pH 7.4, 0.02% thimerosal, 0.1% Triton X-100). The syringes were agitated on a rotary platform shaker at 180 rpm for 3 hours at room temperature in the dark, and the extract was expelled for analysis. Patch extracts were filtered by centrifugation through 0.1 $\mu$m Whatman (Clifton, N.J.) spin filters at 2000×g for 10 min. Extracts were stored at 4° C. in the dark.

RECOVERY FROM SKIN PATCHES

100 μL aliquots of solutions containing pyridinoline and creatinine were placed onto duplicate skin patches. The patches were dried in a vacuum desiccator overnight and then were extracted with 1.0 mL of EB. Samples were analyzed for pyridinoline by EIA and for creatinine using alkaline picrate.

ANALYTICAL METHODS

Pyridinoline. Pyridinoline in sweat was determined by modifying an enzyme immunoassay kit designed to measure pyridinoline in serum (Special Edition Collagen Crosslinks™ Kit; Metra Biosystems, Inc. Mountain View, Calif.). Pyridinoline standards and controls from the kit were diluted 500-fold with extraction buffer. In coated microliter wells, 100 μL (50–200 μL) of standard, control or sample was reacted overnight at 4° C. with 50 μL (25–150 μL) of primary antibody. After washing the wells, 150 μL of second antibody-enzyme conjugate was added. Following one hour incubation at room temperature, the wells were washed and 150 μL of substrate (p-nitrophenol) solution was added. The absorbance at 405 nm was measured in a plate reader (Titertek Multiskan Plus, ICN Biomedicals, Costa Mesa, Calif.) after a one hour incubation.

Deoxypyridinoline. Deoxypyridinoline was detected using two independent analytical approaches. The first was enzyme-linked immunoassay using a monoclonal antibody specific for this bone-loss marker. The manufacturer of the assay kit (Metra Biosystems) has shown the specificity of the antibody. The antibody has an affinity constant for deoxypyridinoline of $3\times10^8$ and shows cross reactivity with pyridinoline of less than 2%. Likewise, the antibody shows negligible cross-reactivity (<2.5%) with incompletely digested bone collagen peptides containing deoxypyridinoline. Deoxypyridinoline has been detected in liquid sweat collected during periods of heat-or exercise-induced sweating. It was measured by immunoassay using a specific monoclonal antibody raised against human deoxypyridinoline isolated from urine (Metra Pyrilinks-D®, Metra Biosystems, Inc.; cf. Gomez et al., 1996).

N-telopeptide. This peptide is a precursor to free cross-links (pyridinoline and deoxypyridinoline) and is derived from bone-collagen. Its concentration in blood and in sweat and urine is thus directly related to the rate of bone resorption. The amount of N-telopeptide was measured in these fluids with a specific monoclonal antibody (Osteomark®, Ostex, Inc.; cf. Rosen et al., 1994). Applicants collected N-telopeptide in sweat by two different methods. First, in two adults and in one male adolescent, N-telopeptide was measured in exercise- and heat-induced liquid sweat (first concentrated by lyophilization) where it ranged between 0.26–0.89 pmoL/mL (=0.04–0.21 pmoL/μmoL $K^+$; $K^+$ was used as a marker of sweat volume, 4 μmoL of $K^+$ being equivalent to 1 ml of liquid sweat). The second method of sweat collection utilized the Osteopatch ™ (Pacific Biometrics, Irvine, Calif.), an absorbent device applied to skin). Extracts of the patches obtained from seven subjects contained 0.08–0.91 pmoL/μmoL $K^+$ of N-telopeptide. Concentrated liquid sweat was used to confirm the presence of N-telopeptide and related bone peptides by HPLC. In all cases, the amounts of bone loss markers were corrected back to the unconcentrated condition, i.e., as it existed in freshly collected liquid sweat.

Creatinine. Creatinine was measured using minor variations of a common clinical method using the Jaffe reaction (alkaline picrate; Metra Biosystems, Mountain View, Calif.). The creatinine standard was diluted 10, 100 and 1000-fold to include the low level of the analyte found in sweat samples. In microliter wells we placed 50 μL of standards or sample and 100 μL alkaline picrate, and absorbance at 492 nm was measured in the Titertek plate reader.

Urea. The urea nitrogen assay kit (Sigma) was used to measure both urea and ammonia in sweat samples, based on the hydrolysis of urea into ammonia and carbon dioxide. The total concentration of urea and ammonia (T) was measured by reacting samples with urease, followed by reaction with hypochlorite and phenol which, in the presence of sodium nitroprusside, forms the blue chromophore, indophenol. Indophenol was quantified by absorbance at 600 nm. Ammonia (A) was measured by omitting urease in the same reaction scheme. The amount of urea in a sample prior to urea hydrolysis (U) was calculated by subtracting the ammonia value from the total value found for both ammonia and urea ($U=T-A$).

Potassium. Potassium in sweat was determined by means of an ion specific electrode (Cole Parmer Instrument Company, Niles, Ill.). The electrode was calibrated against dilutions of a 1.0 g/L potassium standard (Cole Parmer).

Results

Figure 1:
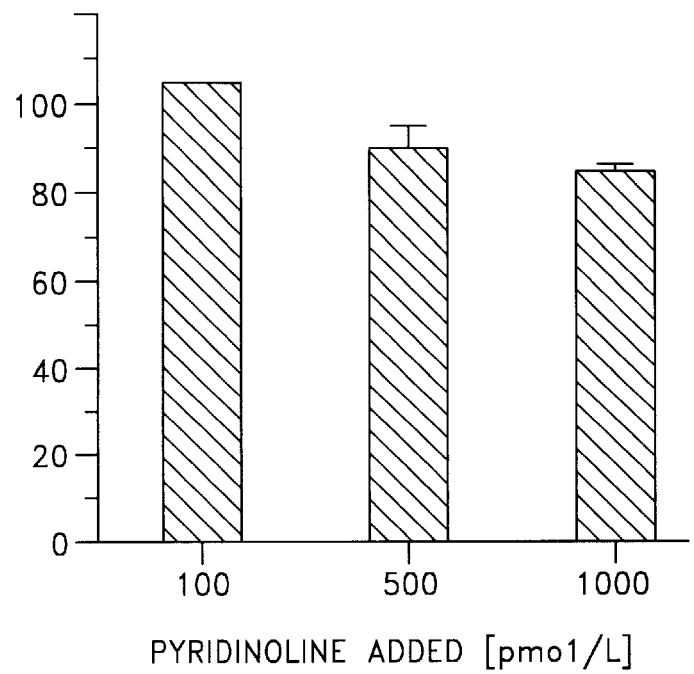
FIG. 1 is a graph showing the extraction recovery of pyridinoline spiked onto a skin patch where pyridinoline was placed on each patch (n=2) at concentrations that approximate 20, 50, and 80% binding in the immunoassay.

Recovery of pyridinoline spiked onto unworn skin patches. Pyridinoline recovery in the patch extracts was nearly quantitative when patches were extracted with EB (FIG. 1). Similar results were obtained using 0.1% Tween 20 instead of Triton X-100 and also when the buffer was omitted. We selected EB as the standard method due to the stabilizing effect of the buffer and the lack of interference of Triton X-100 on the immunoassay (data not shown).

SOURCES OF ASSAY INTERFERENCE

It is possible that artificially low or high levels of pyridinoline or of reference markers was measured due to sample instability, contamination or other assay interference. Significant potential sources of error include: a) photolysis of pyridinoline by ultraviolet light; b) the effect of skin enzymes or bacterial action on analyte levels; and c) the effect of shed epidermis on measurements.

Figure 2:
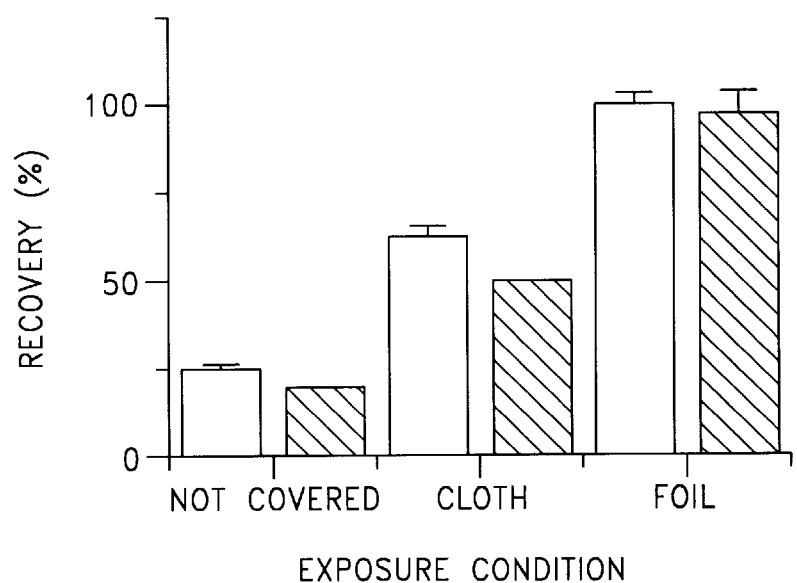
FIG. 2 is a bar graph detailing the effect of sunlight on pyridinoline recovery, pyridinoline was added to duplicate patches at 100 (shaded bars) or 500 fmol/mL (open bars), the data are calculated from the expected recoveries.

Elimination of photolysis. Pyridinoline was spiked onto patches that were then exposed to direct sunlight for 21 hours (FIG. 2). Patches that were shaded by aluminum foil gave no significant loss of analyte. Most pyridinoline in uncovered patches was lost, and covering patches with thin cloth did not completely protect the pyridinoline. Thus, for the purpose of measuring pyridinoline in sweat, the skin patch should include a layer of material that is opaque to ultraviolet light to prevent photolysis of pyridinoline.

Effect of bacterial action. Compounds that accumulate in the skin patch are exposed to conditions that might favor growth of microorganisms.

Figure 3:
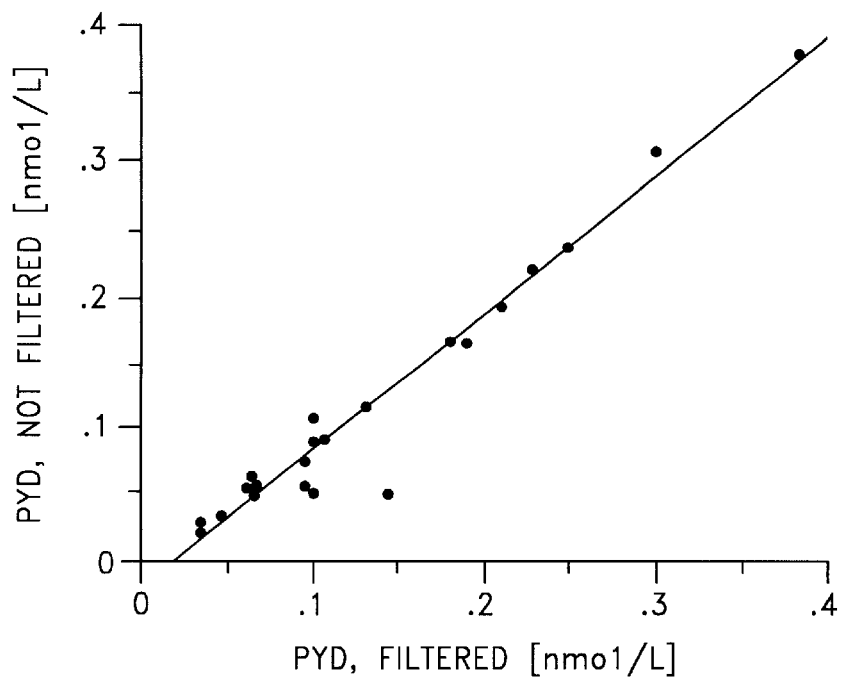
FIG. 3 is a graph showing the effect of sample filtration on measurement of pyridinoline in sweat samples, skin patches worn by volunteers for 1 to 7 days were extracted, extracts were spin filtered (abscissa) or not filtered (ordinate), and pyridinoline was assayed, data from four separate experiments were combined; n=22 samples, regression line: y=−0.014+1.02x; r=0.98.

Effect of cellular debris. Pyridinoline is found in collagen from a variety of tissues, but it has not been found in skin. While there may be no pyridinoline in skin, it is possible that cellular debris collected in the patch will interfere non-specifically in the pyridinoline assay. To test for the presence of such assay interference, skin patches were worn by volunteers, the patches were extracted and aliquots of the extracts were filtered through Whatman nitrocellulose spin filters (0.1 μm) and assayed for pyridinoline. Results of the comparison of filtered and nonfiltered samples (FIG. 3) suggest that there may be no significant assay interference due to protein and cellular debris in the extract; the calculated values average 103% of the measured values for nonfiltered samples.

MEASUREMENT OF MARKERS OF BONE METABOLISM IN SWEAT SAMPLES

Figure 4:
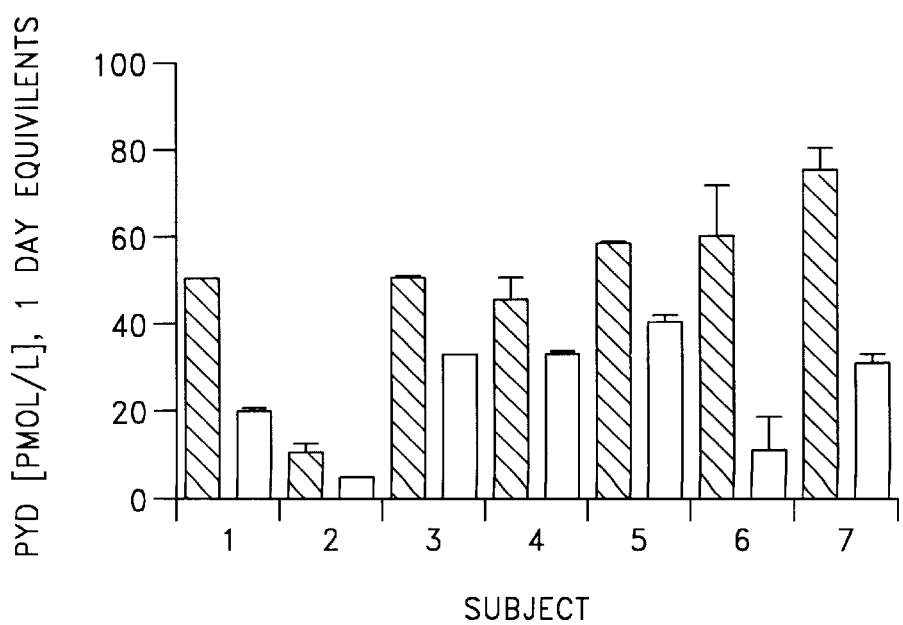
FIG. 4 is a bar graph detailing the recovery of pyridinoline in sweat from different parts of the body, patches were worn simultaneously on the trunk (shaded bars) and extremities for three to five days on each individual and each measurement was made in duplicate.

Pyridinoline levels based on location on the body. Levels of pyridinoline in sweat collected in skin patches worn on the trunk (abdomen and lower back) and on the extremities (upper arms and legs). In all individuals tested, the mass of pyridinoline was greater in patches worn on the trunk than those on the extremities (FIG. 4).

Figure 5:
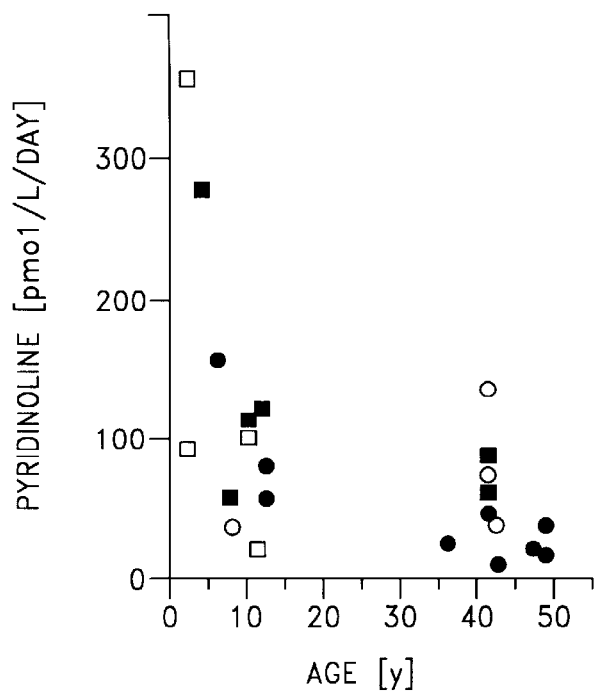
FIG. 5 is a graph detailing the relationship of secretion of pyridinoline as a function of age, patches were worn by 25 individuals, female: circles, male: boxes.

Pyridinoline levels based on age. Levels of pyridinoline measured in sweat collected in from a variety of individuals, ranging in age from 2 to 50 years. In all cases, skin patches were worn on the lower back. The mass of pyridinoline was greater in very young children, and, among adults, highest among females (FIG. 5).

Figure 6:
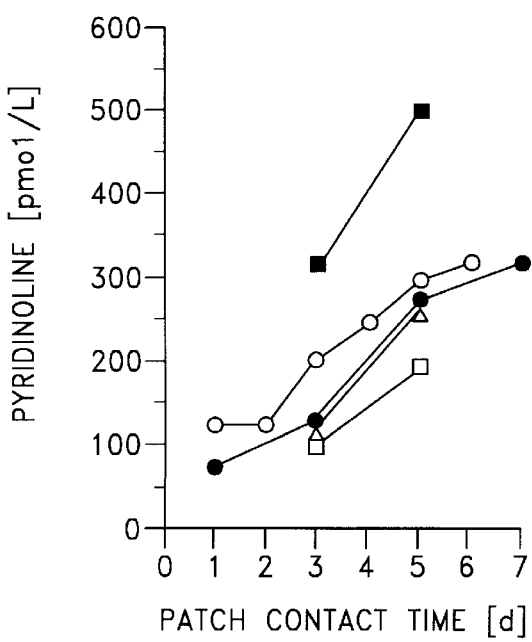
FIG. 6 is a graph showing the relationship of the concentration of pyridinoline as a function of time, pyridinoline collected in skin patches worn for varying lengths of time, patches were worn on the back, extracted and analyzed for pyridinoline.

Pyridinoline levels based patch contact time. Skin patches worn for longer time accumulate a greater mass of pyridinoline (FIG. 6). In all cases, skin patches were worn on the lower back. The rate of accumulation of pyridinoline was similar in many cases.

Because of the relatively low abundance of deoxypyridinoline compared with pyridinoline, it was necessary to concentrate liquid sweat by lyophilization (freeze-drying) prior to assay.

In three volunteers, deoxypyridinoline ranged from 0.14 to 0.24 pmoL/mL (picomol=$10^{-12}$ moL). In one adolescent undergoing rapid bone growth (and therefore, displaying a high rate of bone remodeling), deoxypyridinoline was found to be 0.78 pmoL/mL. The amount of deoxypyridinoline was smaller than the amount of pyridinoline measured in the same samples in accordance with the greater content of pyridinoline in bone collagen.

The presence of deoxypyridinoline was independently confirmed by HPLC (High Performance Liquid Chromatography) using the standard methods developed for the detection of deoxypyridinoline in bone digests and in human urine (Eyre, 1987). In two concentrated sweat samples, deoxypyridinoline by HPLC was 0.23 and 0.50 pmoL/mL. Within the accuracy of the method, these values confirmed the immunoassayable content of sweat. In all cases, the amounts of bone loss markers were corrected back to the unconcentrated condition, i.e., as it existed in freshly collected liquid sweat.

Figure 10:
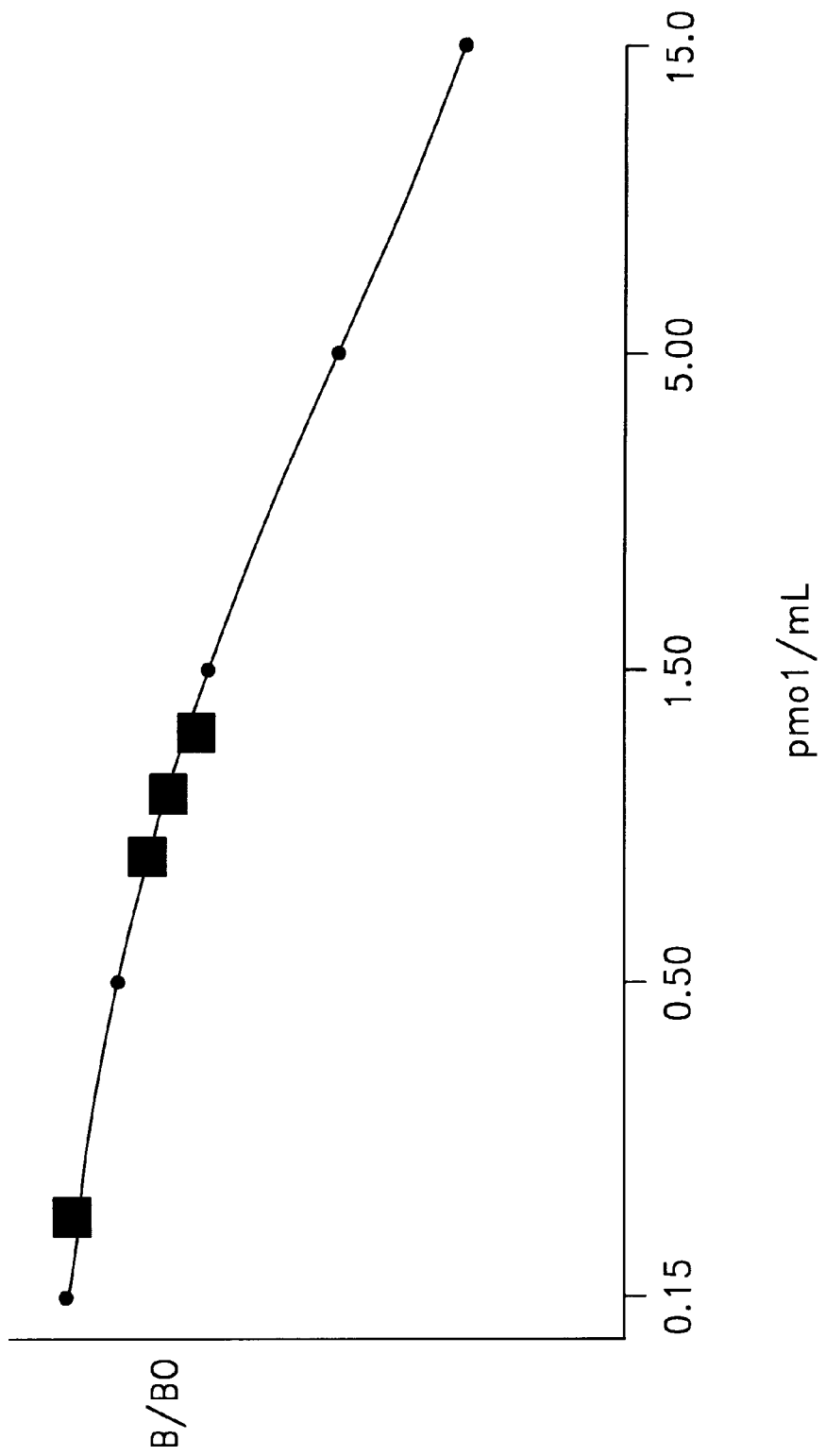
FIG. 10 is a graph illustrating a sensitive deoxypyridinoline immunoassay in which sweat content of the bone loss marker was quantified wherein ■ indicates the location on a standard curve of when four samples of liquid sweat were assayed.

FIG. 10 illustrates the results of a sensitive deoxypyridinoline immunoassay in which sweat content of the bone loss marker was quantified. The abscissa is the concentration of validated standards of deoxypyridinoline provided by Metra Biosystems. The concentration of standards are pmoL/mL (=nM; =$10^{-9}$ M) The ordinate is $B/B_o$, a measure of the specific displacement of assay antigen from the antibody as sample or standard antigen was increased. The square symbols indicate the location on the standard curve of when four samples of liquid sweat were assayed. Three of the samples were concentrated by lyophilization for before assay. The sample showing the lowest deoxypyridinoline value was assayed directly without concentration.

FIG. 11 illustrates two HPLC (High Performance Liquid Chromatography) tracings which confirmed the presence of deoxypyridinoline in sweat by an independent method. HPLC was the reference method for measurement of bone-loss markers in bone digests, serum and urine. The lower chromatogram in each Figure represents the optical density of fractions measured by fluorescence (excitation 295 nm; emission 395 nm). The upper tracing is the optical density in the ultraviolet (205 nm). The pyridinium nucleus of pyridinoline and deoxypyridinoline is fluorescent and, therefore, can be monitored by fluorescence. In this case, the UV recording was done as other (non-fluorescent) compounds in sweat were being sought at.

FIG. 11B shows the presence of two peaks identified as pyridinoline and deoxypyridinoline based on their co-migration with pyridinoline and deoxypyridinoline HPLC standards.

FIG. 11A shows the same sample of sweat re-injected for a second HPLC separation after known amounts of standard pyridinoline and deoxypyridinoline were added (spiked) to the sample. The specific elevation in peak height and peak area of the two peaks indicated that the smaller co-migrating peaks in the lower Figure are bona fide pyridinoline and deoxypyridinoline.

FIG. 12 shows the standard curve in a specific enzyme-linked immunoassay for N-telopeptide (Osteomark, Ostex, Inc.) As in the deoxypyridinoline assay, this is a competitive assay in which increasing amounts of antigen in standards of sample lower the signal ($B/B_o$). The square symbols indicate the location on the standard curve of three concentrated (lyophilized) sweat samples. Also indicated are the extent to which the three samples were concentrated prior to lyophilization.

MEASUREMENT OF REFERENCE MARKERS

Three candidate compounds were selected creatinine, urea and potassium, based on their high concentrations in sweat and relatively constant concentrations at varying sweat rates. It is possible that none of these analytes will suffice as a sweat volume marker, and there are others we might need to test, but this will be known only after sufficient data have been collected. In addition to these analytes, we will test the utility of specific gravity of patch extracts as an index of sweat volume.

Creatinine in sweat. Levels of creatinine in sweat did not increase rapidly with an increase in the length of time a patch was worn (FIG. 7).

Urea in sweat. The mass of urea increased at about the same rate for all individuals tested, leveling off when patches were applied for greater than five days (FIG. 8).

Potassium in sweat. As with urea, the levels of potassium in sweat from several individuals increased with the length a patch was worn, and the accumulation of potassium dropped off when patches were worn for greater than five days (FIG. 9).

The experimental data set forth above provides support for the generic term "markers of bone metabolism" and, therefore, provides sufficient support for broad coverage of all markers of bone metabolism detectable in sweat.

The invention has been described in an illustrative manner, and it is to be understood the terminology used is intended to be in the nature of description rather than of limitation.

Obviously, many modifications and variations of the present invention are possible in light of the above teachings.

REFERENCES CITED

Bettica et al., "Bone-resorption markers galactosyl hydroxylysine, pyridinium crosslinks, and hydroxyproline compared" *Clin. Chem.* 38:2313–8 (1992).

Body et al., "Urinary pyridinium cross-links as markers of bone resorption in tumor-associated hypercalcemia" *J. Clin. Endocrin Metab.* 74:471–5 (1992).

Delmas, PD "Biochemical markers of bone turnover: methodology and clinical use in osteoporosis" *Am. J. Med.* 91 (Supp 5B):59S–63S (1991).

Delmas et al., "Urinary excretion of pyridinoline crosslinks correlates with bone turnover measured on iliac crest biopsy in patients with vertebral osteoporosis" *J. Bone Miner Res.* 6:639–44 (1991).

Eastell et al., "Nyctohemeral changes in bone turnover assessed by serum bone gla-protein concentration and urinary deoxypyridinoline excretion: effects of growth and aging" *Clin. Sci.* 83:375–82 (1992).

Eastell et al., "Abnormalities in circadian patterns of bone resorption and renal calcium conservation in type I osteoporosis" *J. Clin. Endocrin Metab.* 74:487–94 (1992).

Elomaa et al., "Serum concentration of the cross-linked carboxyterminal telopeptide of type I collagen (ICTP) is a useful prognostic indicator in multiple myeloma" *Br. J. Cancer* 66:337–41 (1992).

Eyre, "Collagen cross-linking amino acids in *Methods Enzymol.* 144:115–139 (1987).

Gertz et al., "Monitoring bone resorption in early postmenopausal women by an immunoassay for crosslinked collagen peptides in urine" *J. Bone Min. Res.* 9:135–142 (1994).

Gomez et al., "Monoclonal antibody assay for free urinary pyridinium cross-links, *Clin. Chem.*, 42: 1168–1175 (1996).

Harvey et al., "Measurement of bone collagen degradation in hyperthyroidism and during thyroxine replacement therapy using pyridinium cross-links as specific urinary markers" *J. Clin. Endocrin Metab.* 72:1189–94 (1991).

Robins, et al. "Evaluation of urinary hydroxypridinium crosslink measurements as resorption markers in metabolic bone diseases" *Eur. J. Clin Invest.* 21:310–5 (1991).

Rosen et al., "Specificity of urinary excretion of cross-linked N-telopeptides of Type I collagen as a marker of bone turnover" *Calcif. Tiss. Int.* 54: 26–29 (1994).

Schlemmer et al., "Marked diurnal variation in urinary excretion of pyridinium cross-links in premenopausal women" *J. Clin. Endocrin Metab.* 74:476–80 (1992).

Seibel, et al., "Urinary hydroxypyridinium crosslinks provide indices of cartilage and bone involvement in arthritic diseases" *J. Rheumatol.* 16:964–70 (1989).

We claim:

1. A method of monitoring bone metabolism comprising continuously collecting a sweat sample from a subject and assaying the sweat sample to determine the concentration of a marker of bone metabolism in the sample, wherein said marker is not pyridinoline or deoxypyridinoline.

2. The method of claim 1 further including the step of normalizing the volume of the sweat sample collected.

3. The method of claim 1 wherein said normalizing step further includes quantitatively analyzing the concentration of a reference marker present in the sweat sample, which amount is directly associated with the amount of sweat collected from the subject.

4. The method of claim 3 wherein the reference marker is selected from the group consisting of creatinine, urea, potassium, and other suitable markers.

5. The method of claim 1 wherein the marker of bone metabolism is n-telopeptide.

6. The method of claim 1 wherein the marker of bone metabolism is lysyl pyridinoline.

7. The method of claim 1 wherein the marker of bone metabolism is substituted pyridinoline.

8. The method of claim 1 wherein the marker of bone metabolism is hydroxylysyl pyridinoline.

9. The method of claim 1 wherein the marker of bone metabolism is procollagen Type I and its cleavage products.

10. The method of claim 1 wherein the marker of bone metabolism is osteocalcin.

11. The method of claim 1 wherein said step of collecting sweat further includes applying a sweat collection means to the subject.

12. The method of claim 11 wherein the sweat collection means is selected from the group consisting of a skin patch, an absorbent pad, or a capillary tube.

13. The method of claim 1 further comnrises extracting the marker of bone metabolism from the collected sweat sample.

14. The method of claim 13 wherein said assaying step comprises qualitatively and quantitatively determining the concentration of the marker of bone metabolism.

15. The method of claim 14 wherein the concentration of the marker of bone metabolism is determined by enzyme immunoassay techniques.

16. A method of using a sweat collection device by collecting a sweat sample from a subject wherein the sweat sample contains markers of bone metabolism; and assaying the sweat sample for markers of bone metabolism.

17. A method for determining the volume of secreted sweat over a given period of time by quantitatively determining the concentration of at least one reference marker secreted in sweat collected over the given time period.

18. The method of claim 17, wherein said step of quantitatively determining the concentration of at least one reference marker is further defined as of normalizing the volume of the sweat sample collected.

19. The method of claim 18, wherein said normalizing step further includes quantitatively analyzing the concentration of a reference marker present in the sweat sample, which amount is directly associated with the amount of sweat collected from the subject.

20. The method of claim 19, wherein the reference marker is selected from the group consisting of creatinine, urea, potassium, or other suitable markers.

21. The method of claim 17, wherein said step of collecting a sweat sample includes applying a sweat collection device to the subject.

22. The method of claim 21, wherein the sweat collection device is isolated from the group consisting of a skin patch, an absorbent pad, and a capillary tube.

* * * * *